United States Patent
Vojdani

(10) Patent No.: US 6,492,113 B1
(45) Date of Patent: Dec. 10, 2002

(54) DETECTION OF MYCOPLASMA GENUS AND SPECIES IN PATIENTS WITH CHRONIC FATIGUE SYNDROME AND FIBROMYALGIA

(75) Inventor: Aristo Vojdani, Los Angeles, CA (US)

(73) Assignee: Immunosciences Lab, Inc., Calif. corporation, Beverly Hills, CA (US)

( * ) Notice: Subject to any disclaimer, the term of this patent is extended or adjusted under 35 U.S.C. 154(b) by 0 days.

(21) Appl. No.: 09/283,689

(22) Filed: Apr. 1, 1999

(51) Int. Cl.$^7$ .......................... C12Q 1/68; C12N 15/10; G01N 33/53; G01N 33/573

(52) U.S. Cl. .............................. 435/6; 435/5; 435/7.1; 435/7.21; 435/7.24; 435/7.4; 435/15; 435/7.92; 435/86; 436/86; 530/350; 536/22.1; 536/23.5

(58) Field of Search ........................ 435/5, 6, 7.1, 7.4, 435/7.21, 7.24, 372, 91.2, 792, 15, 86; 436/86; 530/350; 536/22.1, 23.5

(56) References Cited

U.S. PATENT DOCUMENTS

| | | | |
|---|---|---|---|
| 5,627,275 A | 5/1997 | Roll | |
| 5,766,859 A | 6/1998 | Vojdani et al. | 435/7.1 |
| 5,776,690 A | 7/1998 | Vojdani et al. | 435/6 |
| 5,830,668 A | 11/1998 | Mordechai et al. | 435/7.4 |
| 5,853,996 A | 12/1998 | Mordechai et al. | 435/6 |

OTHER PUBLICATIONS

Huang et al., "The prevalence of *Mycoplasma incognitus* in normal controls or patients with aids or the chronic fatigue syndrome", Clinical Infections Diseases, 1997, vol. 25, No. 2, p. 484. Abstract Only.*
Proceedings: American Assoc. For Chronic Fatigue Syndrome Research Conference, Oct. 13 and 14, 1996 (San Francisco) p. 3 "Possible Connection Between *Mycoplasma incognitus* and Dys–Regulation of Cytokine Production in Chronic Fatigue Syndrome" by Aristo Vojdani, et al.
Ginsburg et al., *Ureaplasma urealyticum* and *Mycoplasma hominis* in Women with Systemica Lupus Erythematosus, (1992) Arthritis and Rheumatism vol. 35 No. 4 pp. 429–433.
Nicolson et al., Diagnosis and Treatment of Chronic Mycoplasmal Infections in Fibromyalgia and Chronic Fatigue Syndromes: Relationship to Gulf War Illness (1998) Biomedical Therapy vol. 16 No. 4 p. 266–271.
Nicolson et al., Mycoplasmal Infections and Fibromyalgia/Chronic Fatigue Illness (Gulf War Illness) Associated with Deployment to Operation Desert Storm (1998) Int. Journal of Medicine 1:80–92.
Nicolson et al., Diagnosis and Treatment of Mycoplasmal Infections in Persian Gulf War Illness—CFIDS Patients (1996) Int. Journal of Occuptational Medicine, Immunology and Toxicology vol. 5, No. 1 pp. 69–77.
Bej, et al., Multiplex PCR amplification and immobilized capture probes for detection of bacterial pathogens and indicators in water, *Mol. Cell. Probes* 4:353–365, (1990).
Buchwald, et al., Comparison of Patients With Chronic Fatigue Syndrome, Fibromyalgia, and Multiple Chemical Sensitivities, *Arch. Intern. Med* 154:2049–2053 (1994).
Choppa, et al., Multiplex PCR for the detection of *Mycoplasma fermentans, M. hominis* and *M. penetrans* in cell cultures and blood samples of patients with chronic fatigue syndrome, *Mol. Cell. Probes* 12:301–308 (1998).
Fukuda, et al., The Chronic Fatigue Syndrome: A Comprehensive Approach to Its Definition and Study, *Fed. Pract.* 121:953–959 (1994).
Grau, et al., Development of PCR–based assays for the detection of two human mollicute species, *Mycoplasma penetrans* and *M. hominis, Mol. Cell. Probes* 8:139–148 (1994).
Hawkins, et al., Association of Mycoplasma and Human Immunodeficiency virus Infection: Detection of Amplified *Mycoplasma fermentans* DNA in Blood, *J. Infect. Dis.* 165:581–585 (1992).
Hayes, et al., Pathogenicity of *Mycoplasma fermentans* and *Mycoplasma penetrans* in Experimentally Infected Chicken Embryos, *Infect. Immun.* 64(8):3419–3424 (1996).
Hopert, et al., Specifity and sensitivity of polymerase chain reaction (PCR) in comparison with other methods for the detection of Mycoplasma contamination in cell lines, *J. Immunol. Meth.* 164:91–100 (1993).
Kulski, et al., Use of a Multiplex PCR To Detect and Identify *Mycobacterium avium* and *M. intracellular* in Blood Culture Fluids of AIDS Patients, *J. Cline. Microbial.* 33(3):668–674 (1995).
Mountaineer et al., Mycoplasmas as Cofactors in Infection Due to the Human Immunodeficiency Virus, *Clin. Infect. Dis.* 17(Suppl. 1):S309–315 (1993).
Razin, Shmuel, DNA probes and PCR in diagnosis of Mycoplasma infections, *Mol. Cell. Probes* 8:497–511 (1994).
Schaeverbeke, et al., Systematic Detection of Mycoplasmas by Culture and Polymerase Chain Reaction (PCR) Procedures in 209 Synovial Fluid Samples, *Br. J. Rheumatol.* 36:310–314 (1997).
Straus, Stephen., History of Chronic Fatigue Syndrome, *Rev. Infect. Dis.* 13(Suppl.1)S2–S7 (1991).
van Kuppeveld, et al., Detection of Mycoplasma Contamination in Cell Cultures by a Mycoplasma Group–Specific PCR, *Appl. Environ. Microbiol.* 60:149–152 (1994).
van Kuppeveld, et al., Genus– and Species–Specific Identification of Mycoplasmas by 16S rRNA Amplification, *Appl. Environ. Microbiol.* 58:2606–2615 (1992).
Wang, et al., Multiplex PCR for avian pathogenic mycoplasmas, *Mol. Cell. Probes* 11:211–216 (1997).
Vojdani, et al., Detection of Mycoplasma genus and *Mycoplasma fermentans* by PCR in patients with Chronic Fatigue Syndrome, *FEMS Immunol. and Med. Microbiol.* 22:355–365 (1998).
Ziem, et al., Chronic Fatigue, Fibromyalgia, and Chemical Sensitivity: Overlapping Disorders, *Arch. Intern. Med.* 154:1913 (1995).

* cited by examiner

Primary Examiner—Long V. Le
Assistant Examiner—Lisa V. Cook
(74) Attorney, Agent, or Firm—Knobbe, Martens, Olson & Bear LLP

(57) ABSTRACT

Methods for detecting chronic fatigue syndrome and/or fibromyalgia in an individual, comprising isolating peripheral blood mononuclear cells (PBMC) and: 1) determining the amounts of Mycoplasma genus or Mycoplasma species; 2) determining the Mycoplasma gene copy number; or 3) determining the levels of anti-*M. fermentans* antibodies present in serum, wherein elevated levels of any of these indicate the presence of CFS and/or fibromyalgia.

1 Claim, 3 Drawing Sheets

DETECTION OF MYCOPLASMA GENUS AND SPECIES IN PATIENTS WITH CHRONIC FATIGUE SYNDROME AND FIBROMYALGIA

BACKGROUND OF THE INVENTION

1. Field of the Invention

The present invention relates to a method for determining an increased likelihood of the presence of chronic fatigue syndrome (CFS) in an individual by determining the presence of elevated levels of Mycoplasma DNA in peripheral blood mononuclear cells.

2. Description of the Related Art

Chronic Fatigue Syndrome (CFS) is an illness with increasingly reported frequency in the United States and other industrialized countries (Straus, Rev. Infect. Dis. 13(Suppl. 1):S2–S7, 1991). CFS is characterized by prolonged and debilitating fatigue with multiple non-specific symptoms such as headaches, recurring sore throats, muscle and joint pains and cognitive complaints. Profound fatigue, the hallmark of the disorder, can appear suddenly or gradually and persists throughout the course of the illness. Unlike the short-term disability of an acute viral infection, for example, CFS symptoms by definition linger for at least six months and often for years (Fukuda et al., Ann. Intern. Med. 121:953–959, 1994). Physicians can evaluate patients with persistent fatigue of undetermined cause using guidelines developed by the international CFS study group (Fukuda et al., Fed. Pract. 12:12–17, 1995).

It has been well documented that individuals who suffer from fibromyalgia (FMS) exhibit many of the same symptoms found in atypical CFS (Buchwald et al., Arch. Intern. Med. 154:2049–2053, 1994; Ziem et al., Arch. Intern. Med. 154:1913, 1995) in which a patient has 6 or 7 tender points. These two illnesses are so similar that for years many medical practitioners have considered them to be the same condition.

Despite multidisciplinary investigations of CFS, its etiology remains unknown and no specific diagnostic tests or therapies for CFS exist. In about one third of cases, the sudden onset follows a respiratory, gastrointestinal, or other acute infection with flu-like symptoms, including mononucleosis (Mawle et al., Infect. Agents Dis. 2:333–341, 1994). No published data implicate a specific virus or other microbes as the cause of CFS. However, it appears that infectious agents, among other stressors, can precipitate the syndrome (National Institutes of Health Publication No. 96-484, 1996). A variety of common viruses can be reactivated in some CFS patients, including HTLV-II, Epstein-Barr virus (EBV), cytomegalovirus (CMV), herpes simplex viruses (HSV) 1 and 2, and human herpes viruses 6, 7 and 8. It is believed that virus reactivation could be occurring secondarily to some immunologic disturbance (National Institutes of Health Publication No. 96–484, 1996; Nicolson et al., Int. J. Occup. Med. Immunol. Toxicol. 5:69–78, 1996).

Mycoplasmas are bacteria which belong to the class Mollicutes. They are the smallest free-living, self-replicating bacteria known. They have no cell wall and a very limited genome of between 600 and 1,500 kilobases which makes them highly dependent on their host for survival. The mycoplasma species M. fermentans, M. hominis and M. penetrans have been isolated from individuals suffering from primary atypical pneumonia, urogenital infections, rheumatoid arthritis (RA) and AIDS-related infections (Hayes et al., Infect. Immun. 64:3419–3424, 1996; Schaeverbeke et al., Br. J. Rheumatol. 36:310–314, 1997; Montagnier et al., Clin. Infect. Dis. 17(Suppl. 1):S309–315, 1993).

There is an ongoing need for methods of detecting CFS infection. The present invention addresses this need.

SUMMARY OF THE INVENTION

One embodiment of the present invention is a method for determining an increased likelihood of the presence of chronic fatigue syndrome (CFS) and/or fibromyalgia (FMS) in an individual, comprising the steps of: isolating peripheral blood mononuclear cells (PBMC) from said individual; and determining an amount of a Mycoplasma species present in the PBMC from the individual compared to an amount of Mycoplasma species present in PBMC from a control individual known not to have CFS or FMS, wherein an increase in the amount in the individual compared to the control individual indicates an increased likelihood of the presence of CFS and/or FMS. Preferably, the Mycoplasma species is Mycoplasma fermentans. In one aspect of this preferred embodiment, the determining step comprises detection of Mycoplasma polynucleotides. Preferably, the determining step comprises use of polynucleotide amplification. In another aspect of this preferred embodiment, the determining step comprises amplification of a DNA fragment specific to a plurality of Mycoplasma species. Preferably, the determining step comprises amplification of a 206 base pair fragment specific to Mycoplasma fermentans. In one aspect of this preferred embodiment, the amount of the Mycoplasma species present in PBMC from a control individual known not to have CFS is a mean average of a plurality of control individuals. Preferably, the increase is at least about 25%. More preferably, the increase is at least about two-fold. Most preferably, the increase is at least about three-fold. In one aspect of this preferred embodiment, the amount of Mycoplasma species is calculated as a genome copy number. Preferably, the determining step comprises quantitative competitive PCR. Alternatively, the determining step comprises Southern blotting. Advantageously, the quantitative competitive PCR comprises use of the oligonucleotide primers having sequences shown in SEQ ID NOS: 9 and 10.

The present invention also provides a method for determining an increased likelihood of the presence of chronic fatigue syndrome (CFS) in an individual, comprising the steps of: isolating blood serum from said individual; and determining the amount of anti-Mycoplasma antibodies in blood serum, wherein an increase in the amount compared to a control individual known not to have CFS indicates an increased likelihood of the presence of CFS. Preferably, the determining step comprises enzyme- linked immunosorbent assay. In one aspect of this preferred embodiment, the antibodies are anti-M. fermentans antibodies. Advantageously. the anti-M. fermentans antibodies recognize M. fermentans P29 surface lipoprotein. In another aspect of this preferred embodiment, the amount of antibodies specific to Mycoplasma present in serum from a control individual known not to have CFS is a mean average of a plurality of control individuals. Preferably, the increase is at least about 25%. More preferably, the increase is at least about two-fold. Most preferably, the increase is at least about three-fold.

DETAILED DESCRIPTION OF THE PREFERRED EMBODIMENTS

Figures 1A, 1B:
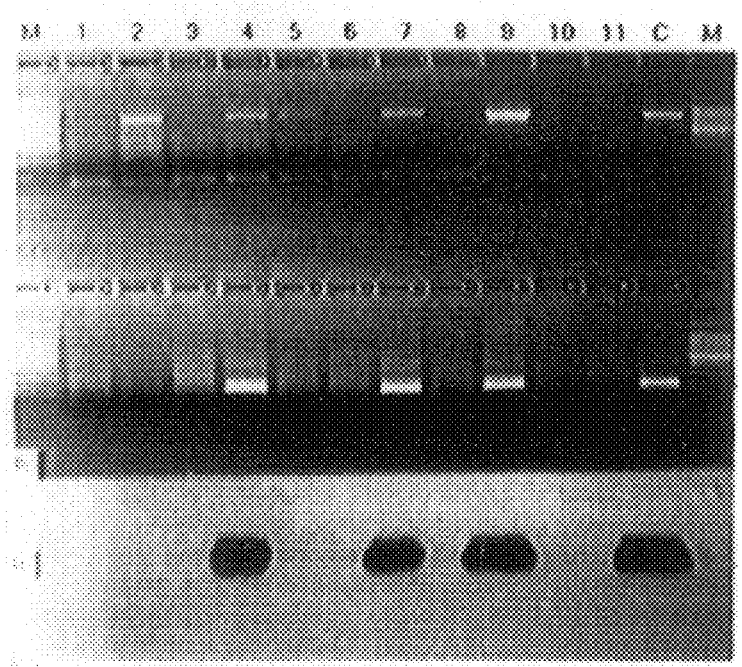
FIG. 1A is a 1.5% ethidium bromide-stained agarose gel showing detection of Mycoplasma genus and M. fermentans in blood samples of patients with CFs. Lane M=DNA size marker and lane C=positive controls containing 5 pg of Mycoplasma genus (717 bp) and M. fermentans. Lanes 4, 7 and 9 are positive for both Mycoplasma genus and M. fermentans.
FIG. 1B is a Southern blot analysis of M. fermentans in each lane shown in FIG. 1A. Lane C=control M. fermentans DNA; Lanes 4, 7 and 9 are representative of positive samples.

The present invention provides methods for determining an increased likelihood of the presence of chronic fatigue syndrome (CFS) and/or fibromyalgia (FMS) by determining the presence of elevated levels of Mycoplasma genus and/or a Mycoplasma species in peripheral blood mononuclear cells (PBMCs) compared to individuals known not to have CFS or FMS by methods including polymerase chain reaction (PCR) and Southern hybridization. In a preferred embodiment, the Mycoplasma species which is detected is *M. fermentans*, although any other species can also be detected by amplifying a region of the genome specific to the species of interest. For example, *M. hominis* can be detected using the primers 5'-ATACATGCATGTCGAGCGAG-3' (SEQ ID NO: 1) and 5'-CATCTTTAGTGGCGCCTTAC-3' (SEQ ID NO: 2) (Grau et al., *Mol. Cell. Probes* 8:139–148, 1994). One or more unique regions of the genome of any Mycoplasma species which can be specifically amplified can easily be determined if the genome sequence is known and compared to other known genomic sequences by standard sequence alignment programs.

It is contemplated that any nucleic acid amplification method, preferably PCR-based amplification methods, can be used, including reverse transcriptase PCR (RT-PCR), quantitative competitive PCR (QC-PCR) and any other modified PCR, to detect the presence of Mycoplasma DNA or RNA. CFS was also detected by determining the number of *M. fermentans* genome copies present in PBMC by methods including quantitative competitive PCR (QC-PCR) and quantitative dot blot analysis. In addition, CFS is detected by increased levels of antibodies to *M. fermentans* in blood serum using any conventional immunoassay such as enzyme-linked immunosorbent assay (ELISA), radioimmunoassay and immunoblotting. In this method, blood serum is isolated from an individual and the amount of anti-Mycoplasma antibodies in blood serum is determined, wherein an increase in the amount compared to a control individual known not to have CFS indicates an increased likelihood of the presence of CFS. In a preferred embodiment, the amount of antibodies specific to Mycoplasma present in serum from a control individual known not to have CFS is a mean average of a plurality of control individuals. It is contemplated that the increase is at least about 25%, preferably at least about two-fold and more preferably at least about three-fold.

The present method can be combined with one or more other methods for determining an increased likelihood of the presence of CFS to increase the certainty of diagnosis thereof. Such methods include those described in U.S. Pat. No. 5,776,690, 5, 766, 859, 5,830,668, and 5,853,996, the entire contents of which are hereby incorporated by reference.

While many infections agents have been described in different percentages of patients with CFS, the association of Mycoplasma with CFS infection has not been described. This is the subject of the present invention. A PCR-based assay was used to detect Mycoplasma genus and *M. fermentans* genomes in PBMCs of patients with classical CFS (based on CDC criteria) and CFS patients who, in addition to CDC classification, had 6 or 7 tender points (atypical CFS—CFS plus fibromyalgia). Blood was collected from 100 patients with CFS and 50 control subjects. The amplified products of 717 base pairs (bp) of Mycoplasma genus, and 206 bp of *M. fermentans*, were detected in DNA purified from blood samples in 52% and 34% of CFS patients, respectively. In contrast, these genomes were found on only 14% and 8% of healthy control subjects, respectively ($P<0.0001$). All samples were confirmed by Southern blot with a specific probe based on internal sequences of the expected amplification product. Although a 717 bp region of Mycoplasma genus was amplified by PCR, the amplification of any region of the Mycoplasma genome which is common to all mycoplasma species is within the scope of the present invention. Similarly, the amplification of any region of the *M. fermentans* genome unique to *M. fermentans* is contemplated for use in the methods of the present invention.

While the number and percentage of specimens positive by PCR for Mycoplasma genus and *M. fermentans* were not significantly different in both CFS groups (CFS and CFS plus fibromyalgia), the overall percent positives in CFS and CFS plus fibromyalgia groups was 3–4 fold higher than control individuals.

Phylogenetically closely related and non-related microorganisms were studied for the exclusions of possible cross reaction of the primers used in the PCR assay. *M. fermentans* primers did not form products with other mycoplasmas including *M. hominis* and *M. orale*, indicating specificity of the PCR assay. No PCR results were observed which were positive for *M. fermentans* genome, but negative for Mycoplasma genus. In contrast, many specimens were positive for Mycoplasma genus, but negative for *M. fermentans*, indicating that other mycoplasma species are present in PBMC of patients with CFS.

A quantitative competitive PCR was developed to determine the number of *M. fermentans* genome copies present in 1 $\mu$g of DNA for control and CFS patients. Mycoplasma copy numbers ranging from 0 to 880 and from 264 to 2400 were detected in control and CFS positive subjects, respectively. The difference in the average mycoplasma load between CFS and non-CFS PCR positive samples was not found to have any correlation with the manifestation or severity of clinical symptomatologies associated with CFS.

An enzyme immunoassay was applied for the detection of antibodies against p29 surface lipoprotein of *M. fermentans* to determine the relationship between *M. fermentans* genome copy numbers and antibody levels. Individuals with high genome copy numbers exhibited higher IgG and IgM antibodies against *M. fermentans* specific peptides.

EXAMPLE 1

Patient Selection

A total of 100 CFS patients consisting of 56 females and 44 males, with a median age of 49 (23–65) were chosen for this study according to a case definition of CFS established by the Center for Disease Control (CDC) (Fukuda et al., Ann. Intern. Med. 121:953–959, 1994). This clinical evaluation and classification was performed based on: (i) history and physical examination; (ii) mental status examination; and (iii) laboratory tests to exclude other diagnoses. Patients were determined to have CFS based on the following criteria established by the CDC:

1. Unexplained persistent or relapsing fatigue of new or definite onset that is not due to ongoing exertion, that is not relieved by rest, and that results in a substantial reduction in previous levels of activity.
2. Four or more of the following symptoms concurrently for six months or longer: (a) impaired memory or concentrations were enough to reduce levels of occupational, social. or personal activities; (b) sore throat; (c) tender cervical or axillary lymph nodes; (d) muscle pain; (e) multiple pain without joint swelling or redness; (f) new headaches; (g) unrefreshing sleep; (h) post-exertion malaise lasting more than 24 hours.

Patients were classified as atypical CFS or CFS with fibromyalgia if, in addition to the above criteria, they had 6 or 7 tender points. Each patient had been ill for at least one year. Out of 100 CFS subjects, 78% were Caucasian; 12% were African-American; and 10% were Asian. Racial background did not affect the results. Control subjects (n=50) from the same geographical area, with similar age and race distribution, were chosen from individuals who went to different clinics for yearly checkups and did not have any of the above symptoms for CFS. Blood samples were obtained from all participants by their examining physicians in sterile 10 ml tubes containing ACD (acid citrate dextrose) solution A (Becton-Dickinson). Control specimens were drawn under similar conditions. All samples were shipped at ambient temperatures and delivered within 24 hours from the time the blood was drawn.

EXAMPLE 2

Mycoplasma Strains and Isolation of DNA

The following Mycoplasma strains were obtained from the American Type Culture Collection (ATCC), Rockville, Md.: M. fermentans (ATCC 19989), M. hominis (ATCC 23114) and M. orale (ATCC 23714). DNA was prepared by phenol-chloroform extraction following a two-hour incubation at 55° C. in 1 M Tris HCl, pH 8.0, 0.5 M EDTA (TE) buffer, containing 1% SDS and 50 μg/ml proteinase K. DNA was precipitated in ethanol and resuspended in TE buffer. M. fermentans DNA was quantitated spectrophotometrically and used to prepare positive controls of known mycoplasma cell copy numbers ranging from 0 to 1,000 copies/μl. The DNA extracted from each of the Mycoplasma species served as positive controls for the Mycoplasma genus PCR and was also used to determine the specificity of the M. fermentans PCR. In addition, human lung carcinoma cell line, Staphylococcus pasteurii, B. subtilis, Enterococcus faecalis, Streptococcus sp., Clostridium difficile, Clostridium perfringens, Clostridium ramosum, Clostridium innocuum, Rhodococcus sp., E. coli, Saccharomyces cerevisiae, Candida albicans, and Aspergillus flavus were all obtained from ATCC and used as controls in the PCR assay.

PBMC were isolated using Ficoll-Hypaque density gradient ultracentrifugation (Histopaque; Sigma, St. Louis, Mo.). PBMC were lysed in 1 M Tris HCl, pH 8.5, 0.5 M EDTA, 1% SDS and 50 μg/ml proteinase K. Phenol-chloroform extraction was followed by precipitation with 3 M sodium acetate and 95% ethanol. DNA was pelleted and resuspended to a final concentration of 0.2 mg/ml using TE buffer. This DNA extraction method yielded between 40 and 50 μg DNA from 10 ml blood.

EXAMPLE 3

PCR Amplification of Mycoplasma Sequences

Amplification of mycoplasmal 16S rRNA sequences, which can identify mycoplasmas at both the genus and species levels, were used for PCR reactions (Weisburg et al., J. Bacteriol. 171:6455–6467, 1989; Rawadi et al., PCR Methods Appl. 4:199–208, 1995; Wang et la., J. Clin. Microbiol. 30:245–248, 1992; Hawkins et al., J. Infect. Dis. 165:581–585, 1992). Computer alignment studies of these rRNA sequences have revealed the existence of regions that display sequence variability at the genus and species levels. The unique sequence features which have been extensively described allow for the selection of genus- and species-specific primers for PCR. For the amplification of rDNA sequences, without prior transcription of the rRNA to cDNA, the PCR assay was performed in 100 μl of reaction mixture containing 10 mM Tris HCl, pH 8.3, 50 mM KCl, 2.5 mm $MgCl_2$, 0.01% gelatin, 200 μM dNTP, 2.5 units of Taq DNA polymerase and 50 pmol of each Mycoplasma genus primer: 5'-ACTCCTACGGGAGGCAGCAGTA-3' (SEQ ID NO: 3) and 5'-TGCACCATCTGTCACTCTGTTAACCTC-3' (SEQ ID NO: 4) (Rawadi et al., supra.), which amplify a 717 bp region from the genome of each member of the genus Mycoplasma.

To prevent non-specific annealing of the primers, the DNA was always added last, while the reaction mixture was kept at 94° C. The reaction mixtures were placed in a GENE AMP 9600 thermal cycler (Perkin Elmer). The thermal profile involved an initial denaturation step at 94° C. for 3 min followed by 40 cycles of denaturation at 94° C. for 1 min and primer extension at 72° C. for 2 min. The cycling was followed by a final extension step at 72° C. for 10 min. To prevent contamination, a strict spatial separation of the different technical steps involved in PCR was maintained.

For identification of M. fermentans, each reaction was performed in a final volume of 100μl containing 1 μg sample DNA, 10 μl of 10×PCR buffer (Amersham, Arlington Heights, Ill.), 2.5 mM $MgCl_2$, each dNTP at 200 μM, 2.5 units Taq DNA polymerase and 50 pmol of the following oligonucleotide primers: 5'-GGACTATTGTCTAAACAATTTCCC-3' (SEQ ID NO: 5) and 5'-GGTTATTCGATTTCTAAATCGCCT-3' (SEQ ID NO: 6) (Research Genetics, Huntsville, Ala.). These primers flank a 206 bp region in the M. fermentans genome (Wang et al., supra.; Hawkins et al., supra.). The samples were placed in the same thermal cycler and heated to 94° C. for 3 minutes. The cycling profile consisted of 45 cycles of 94° C., 56° C. and 72° C. for 35 s, 45 s, and 1 min, respectively. The cycling was followed by a final extension step at 72° C. for 10 min. Aliquots of amplified samples (20 μl) were analyzed by electrophoresis on a 1.5% agarose gel stained with ethidium bromide.

PBMC isolated from 100 patients with CFS (50 with typical and 50 with atypical) and 50 control subjects were used for the detection of Mycoplasma genus and M. fermentans by PCR. The oligonucleotide primers are highly specific since no amplification product was detected from the following microorganisms under the same PCR conditions: Staphylococcus pasteurii, B. subtilis, Enterococcus

*faecalis*, Streptococcus sp., *Clostridium difficile, Clostridium perfringens, Clostridium ramosum, Clostridium innocuum*, Rhodococcus sp., *E. coli, Saccharomyces cerevisiae, Candida albicans*, and *Aspergillus fiavus*.

To verify the sensitivity of the PCR, genomic DNA from *M. hominis, M. orale, E. coli* and human carcinoma cell line HTB119 were added to the amplification reaction mixture essentially as described by Berg et al. (supra.). Aliquots of 1 μg of DNA extracted from *M. hominis, M. orale, E. coli* or human carcinoma cell line HTB119 were mixed with serial dilutions of *M. fermentans* DNA, and amplification was performed as described above. The PCR sensitivity was not affected under these conditions, as the expected 206 bp amplification product from the reaction mixture was detected by both agarose gel electrophoresis and dot blot.

The same conditions were then applied to 11 blood samples from patients with CFS. The PCR results are shown in FIG. 1A. A 717 bp band corresponding to Mycoplasma genus DNA was detected in the PCR positive control samples, as well as in five CFS patients. The 206 bp band from *M. fermentans* was detected in three of these five Mycoplasma genus-positive CFS patients, and was confirmed by Southern blot analysis (FIG. 1B). Thus, two of the five CFS patients were positive for Mycoplasma genus, but not for *m. fermentans*.

This qualitative PCR for Mycoplasma genus and *M. fermentans* was then applied to all of the blood samples from patients and controls. The data summarized in Table 1 show that Mycoplasma genus and *M. fermentans* genomes were detected at much higher frequencies in CFS than in control subjects. In the control group, 7 out of 50 (14%) and 4 out of 50 samples (8%) were positive by PCR for Mycoplasma genus and *M. fermentans* genomes, respectively. The percentage of positive mycoplasma genomes was 3.6–4 fold higher in patients with CFS, respectively (Table 1). These differences between the patients compared to the control subjects was statistically significant (P<0.0001).

TABLE 1

Percentage of Mycoplasma genus and *M. fermentans* in patients with CFS and control subjects

| Specimens | Number and percentage of specimens positive by PCR for | |
|---|---|---|
| | Mycoplasma genus | *M. fermentans* |
| Control subjects (n = 50) | 7 (14%) | 4 (8%) |
| Typical CFS patients (n = 50) | 27 (54%) | 18 (36%) |
| Atypical CFS patients* (CFS plus FMS) | 25 (50%) | 16 (32%) |
| Mean | 52% | 34% |

*Typical CFS patients with 6 or 7 tender points found in fibromyalgia.

EXAMPLE 4

Southern Blot Analysis

For confirmation of PCR results, Southern blot analysis was used. The amplified PCR products were transferred to nylon filters in 0.4 N NaOH, crosslinked under ultraviolet light and washed with 2×SSC (standard saline citrate). Filters were then prehybridized for 2 h at 68° C. Filters were then hybridized for 24 hours in 2.5 ml/100 cm² hybridization solution containing 5×SSC, blocking reagent, 0.5% (w/v) (Boehringer-Mannheim, Indianapolis, Ind.), N-lauroylsarcosine, sodium salt, 0. 1% (w/v), 0.02% SDS, 450 ng of denatured salmon sperm DNA and 150 ng of a 73 bp labeled DNA probe which was generated as described by Hawkins et al. (supra.). This probe was generated using the PCR reaction with primers 5'-GATGAGTGTATTGTCATCC-3' (SEQ ID NO: 7) and 5'-AACGTAGAAGAGAATGGC-3' (SEQ ID NO: 8) which were internal to those used for the targeted DNA sequence described above. The prove was labeled with psoralen biotin using the rad-free system (Schleicher & Schuell, Keene, N.H.). After hybridization, filters were washed with 2×SSC, 0.1% SDS (2×5 min at room temperature), followed by 2×SSC containing 0.1% SDS (2×15 min at 68° C.). Hybrids were detected using Lumi-phos 530 chemiluminescent substrate sheet. Gel electrophoresis/Southern blot reactions were positive if a band was noted on the gel and hybridization occurred on the nylon membrane (Berg et al., *Mol. Cell. Probes* 10:7–14, 1996).

EXAMPLE 5

Quantitative Competitive PCR

In order to quantitate the number of infectious agents present in 1 μg of DNA, a quantitative competitive PCR (QC-PCR) assay was developed in which the same sets of primers from *M. fermentans* and the control DNA were constructed by the addition of a neutral DNA fragment of 348 bp. Positive samples were subjected to a second round of amplification using the reaction conditions previously described. The only change in the reaction components was the addition of a neutral DNA fragment of 348 bp flanked by the same target sequences as the mycoplasma 206 bp fragment. The control DNA was constructed as described by the manufacturer using the PCR mimic construction kit (Clontech, Palo Alto, Calif.) and a set of composite primers which contain the target primer sequences: 5'-GGACTATTGTCTAAACAATTTCCCCGCAAGTGA AA-TCTCCTCCG-3' (SEQ ID NO: 9) and 5'-GG TTAT-TCGATTTCTAAATCGCCTGGGACAAGATACT CATCTGC-3' (SEQ ID NO: 10). Once the quantity of control DNA was determined by ethidium bromide staining and spectrophotometrically, serial dilutions were prepared and added to the reaction mixtures in a range of 0–1×10⁴ molecules per tube. The quantity of mycoplasma DNA was determined by densitometry, construction of the standard curve and finding the molecular concentration of the unknown.

Figure 2:
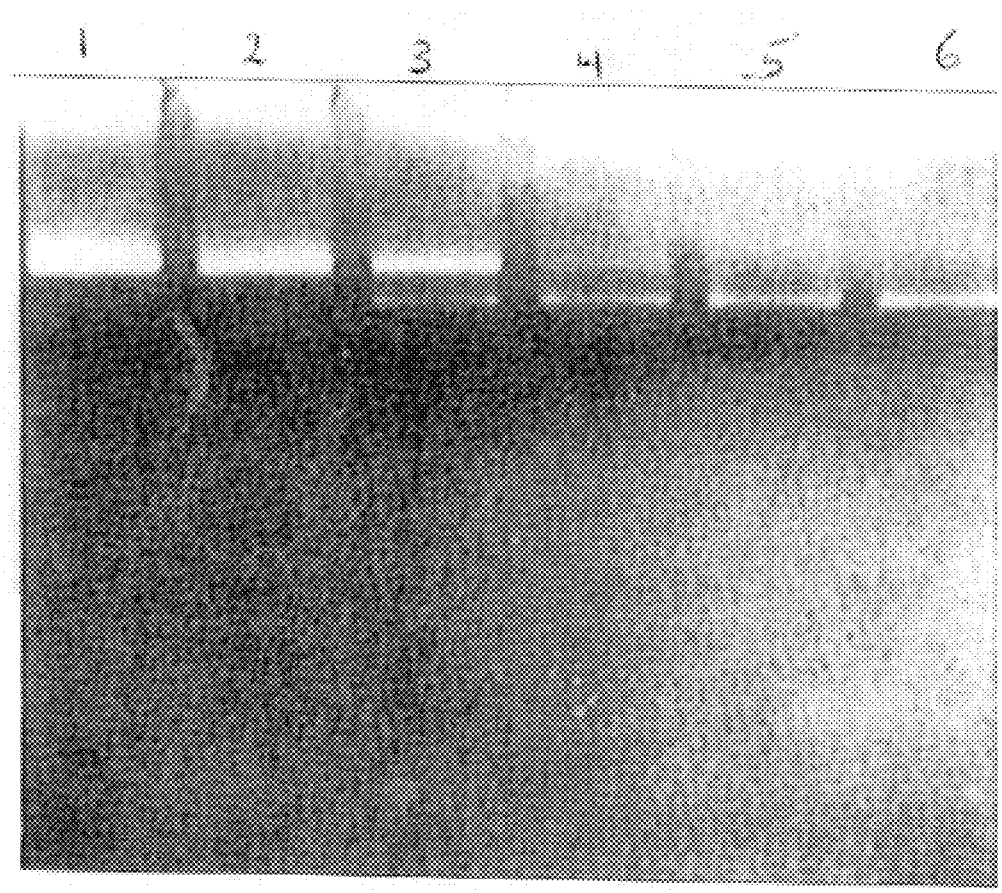
FIG. 2 is an agarose gel of a quantitative competitive PCR result from a mycoplasma positive CFS patient. The internal control of 348 bp is present at 5000, 2500, 1000, 500, 250 and 0 copies in lanes 1–6, respectively. The 206 bp product from the *M. fermentans* genome is increasingly visible in lanes 1–6. The point at which the molar concentration of the internal control and the target product are equivalent by densitometry is used to determine the mycoplasma cell copy number.
Figure 3:
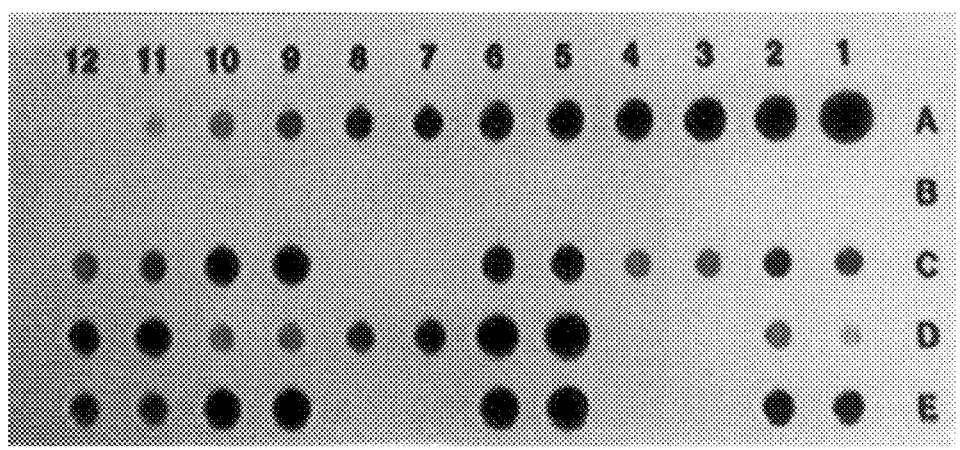
FIG. 3 shows a Southern dot blot analysis of *M. fermentans* genome copy numbers of controls and CFS patients from Table 2 with different genome copy numbers. Rows A1–A12 represent the *M. fermentans* quantitation ladder for calculation of genome copy number. A1=5,000; A2=2,500; A3=1,250; A4=1,000; A5=750; A6=500; A7=400; A8=300; A9=200; A10=100; A11=50; A12=0. Standard curve was generated and the calculated results for the clinical specimens were: rows C1, 2=620; C3, 4=310' C5,6=810; C7,8= negative; C9,10=950; D1,2=150; D3,4=negative; D5,6=230; D7,8=680; D9,10=240; D11,12=860; E1,2=840; E3,4= negative; E5,6=1720; E7,8=negative; E9,10=1550; E11,12= negative.

The results (FIG. 2) show that one CFS patient had 870 copies of *M. fermentans* genome per μg DNA extracted from about 2×10⁵ white blood cells. Using a similar curve, mycoplasma cell copy numbers from 10 CFS patients and four controls who were positive for *M. fermentans* were quantitated. The data are shown in Table 2. The mean average±standard deviation of *M. fermentans* genome copy number for the CFS group and control subjects No. 1–4 was 1052±694 and 522±315, respectively. However, when all 10 control subjects are taken into consideration, the mean average of *M. fermentans* gene copy number is 209. All CFS patients exhibited an increase in *M. fermentans* gene copy number of at least about 25% since the lowest gene copy number in CFS patients was 265 which is about 25% greater than 209. Thus, only three of the control subjects would be determined to have an increased likelihood of the presence of CFS using this test. The remaining seven individuals, as well as all ten of the CFS patients, would be considered to have an increased likelihood of the presence of CFS. Thus, the method correctly detected an increased likelihood of the presence of CFS in 17/20 individuals described in Table 2 who have *M. fermentans* genome copy numbers at least about 25% greater than the mean average of control individuals.

In another preferred embodiment, the increase in Mycoplasma species gene copy number in the CFS individual compared to the mean average of the genome copy number from a plurality of control individuals is about two-fold, more preferably about three-fold.

E9,10=1550; E11,12=negative. Calculated results from the dot blot quantitation were not significantly different from the QC-PCR results, indicating a correlation between the two assays.

EXAMPLE 7

Detection of Anti-*M. fermentans* Antibodies

The specificity of the positive signal detected in the PCR assay was confirmed using *M. fermentans* lysate and two

TABLE 2

*M. fermentans* genome copy number per μg DNA and antibodies

| | Control subjects | | | | | | CFS Patients | | | | | |
|---|---|---|---|---|---|---|---|---|---|---|---|---|
| | | IgG against (OD) | | IgM against (OD) | | | | IgG against (OD) | | | IgM against (OD) | |
| | Genome Number | Lysate | Peptide 1 | Peptide 2 | Lysate | Peptide 1 | Peptide 2 | Genome Number | Lysate | Peptide 1 | Peptide 2 | Lysate | Peptide 1 | Peptide 2 |
| 1 | 130 | 0.25 | 0.16 | 0.19 | 0.36 | 0.21 | 0.19 | 600 | 0.86 | 0.32 | 0.36 | 0.78 | 0.42 | 0.35 |
| 2 | 450 | 0.34 | 0.18 | 0.15 | 0.39 | 0.28 | 0.23 | 1000 | 0.79 | 0.41 | 0.38 | 0.62 | 0.51 | 0.46 |
| 3 | 880 | 0.38 | 0.23 | 0..25 | 0.31 | 0..29 | 0.25 | 2400 | 0.98 | 0.63 | 0.52 | 1.12 | 0.86 | 0.79 |
| 4 | 630 | 0.21 | 0.20 | 0.24 | 0.46 | 0.17 | 0.22 | 320 | 0.61 | 0.21 | 0.34 | 0.49 | 0.27 | 0.22 |
| 5 | N | 0.37 | 0.17 | 0.19 | 0.42 | 0.16 | 0.18 | 910 | 0.57 | 0.33 | 0.29 | 0.57 | 0.35 | 0.30 |
| 6 | N | 0.31 | 0.11 | 0.15 | 0.53 | 0.21 | 0.24 | 1640 | 1.27 | 0.58 | 0.64 | 0.91 | 0.64 | 0.42 |
| 7 | N | 0.41 | 0.20 | 0.23 | 0.34 | 0.18 | 0.26 | 870 | 0.64 | 0.36 | 0.27 | 0.89 | 0.27 | 0.32 |
| 8 | N | 0.22 | 0.15 | 0.21 | 0.32 | 0.17 | 0.22 | 1840 | 0.92 | 0.71 | 0.65 | 0.83 | 0.46 | 0.74 |
| 9 | N | 0.48 | 0.23 | 0.22 | 0.44 | 0.29 | 0.25 | 680 | 0.47 | 0.33 | 0.41 | 0.61 | 0.22 | 0.19 |
| 10 | N | 0.26 | 0.19 | 0.24 | 0.41 | 0.18 | 0.23 | 265 | 0.71 | 0.24 | 0.21 | 0.50 | 0.34 | 0.28 |
| Mean ± | 522.5 | 0.32 | 0.18 | 0.21 | 0.39 | 0.21 | 0.23 | 1052 | 0.78 | 0.41 | 0.41 | 0.73 | 0.44 | 0.41 |
| S.D. | 315.5 | 0.09 | 0.04 | 0.04 | 0.07 | 0.04 | 0.03 | 694 | 0.24 | 0.17 | 0.15 | 0.21 | 0.20 | 0.21 |

EXAMPLE 6

Quantitative Dot Blot Assay

Southern blot analyses of the PCR product shown in Table 2 were confirmed using *M. fermentans* positive control quantitation ladder. A quantitative dot blot assay was used to verify the results of the QC-PCR. Known quantities of purified *M. fermentans* DNA were added to human genomic DNA which was previously determined to be negative for all mycoplasma species by PCR. The mycoplasma DNA was added to negative control DNA ranging from 0 to 5,000 copies per μg of human genomic DNA to serve as a quantitation control ladder. These samples were subjected to the *M. fermentans* specific PCR along with CFS and non-CFS DNA samples in duplicate. The entire 100 μl volume of each PCR reaction tube was blotted on a nylon membrane using a Bio-Rad (Hercules, Calif.) dot blot apparatus. The membrane was then probed by the method described for the Southern blot. The signals from the dot blot assay following hybridization with the *M. fermentans* probe were analyzed by densitometry. The unknown CFS and non-CFS mycoplasma positive samples were plotted against a standard curve generated from the quantitation control ladder signals. The average densities of the duplicate signals from each sample were used to extrapolate the mycoplasma cell copy numbers which are shown in FIG. 1.

Rows A1–A12 represent the *M. fermentans* quantitation ladder for calculation of genome copy number. A1=5,000; A2=2,500; A3=1,250; A4=1,000; A5=750; A6=500; A7=400; A8=300; A9=200; A10=100; A11=50; A12=0. Standard curve was generated and the calculated results for the clinical specimens were: rows C1, 2=620; C3, 4=310' C5,6=810; C7,8=negative; C9,10=950; D1,2=150; D3,4= negative; D5,6=230; D7,8=680; D9,10=240; D11, 12=860; E1,2=840; E3,4=negative; E5,6=1720; E7,8=negative;

specific peptides from the P29 surface lipoprotein sequence. Two peptides from the P29 surface lipoprotein cDNA sequence of *M. fermentans* PG18 or incognitus strain which originally was cultivated from an HIV-positive individual (Lo et al., *Am. J. Trop. Med Hyg.* 41:586–600, 1989) were used in an enzyme linked immunosorbent assay (ELISA). These peptides were chosen from two different regions of the cloned and sequenced P29 gene (Theiss et al., *Infect. Immun.* 64:1800–1809, 1996), and were synthesized by Research Genetics. The peptides were analyzed for purity by mass spectroscopy and were 78% and 81% pure, respectively. Different microtiter wells were coated with 1 μg of each peptide and an indirect ELISA was used to measure IgG and IgM antibody levels in control and CFS patients' sera. A similar ELISA was applied to these sera using *M. fermentans* lysate as a crude antigen.

Overall, IgG and IgM levels against all three antigens were higher in CFS patients than in control subjects. Moreover, patients 3, 6 and 8 (Table 2) with genome copy numbers of 2400, 1640, and 1840, respectively, showed the highest levels of IgG and IgM against the lysate as well as the *M. fermentans* specific peptides. While IgG and IgM optical densities against *M. fermentans* lysate in some control subjects were at least twice as great as the ELISA background (about 0.2) reading, none of the controls, including the four with positive genome copy numbers, had significant elevation in IgG and IgM antibodies against *M. fermentans* peptides. The difference between the optical densities for IgG and IgM against *M. fermentans* in samples from CFS patients who were negative for *M. fermentans* by PCR were not statistically significant from non-CFS patients who were also PCR negative.

It should be noted that the present invention is not limited to only those embodiments described in the Detailed Description. Any embodiment that retains the spirit of the present invention should be considered to be within its scope. However, the invention is only limited by the scope of the following claims.

What is claimed is:

1. A method for determining an increased likelihood of the presence of chronic fatigue syndrome (CFS) in an individual, comprising the steps of:

isolating peripheral blood mononuclear cells (PBMC) from said individual;

determining a quantified amount of a Mycoplasma species present in said PBMC from said individual as a genome copy number by using quantitative competitive PCR using oligonucleotide primers having sequences shown in SEQ IDS: 9 and 10; and comparing said quantified amount to a quantified amount of said Mycoplasma species present in PBMC from a control individual known not to have CFS;

wherein an elevation in said quantified amount in said individual compared to said quantified amount in said control individual indicates an increased likelihood of the presence of CFS.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 1
atacatgcat gtcgagcgag                                                     20

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 2
catcttttag tggcgcctta c                                                   21

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 3
actcctacgg gaggcagcag ta                                                  22

<210> SEQ ID NO 4
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 4
tgcaccatct gtcactctgt taacctc                                             27

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 5
ggactattgt ctaaacaatt tccc                                                24

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 6
ggttattcga tttctaaatc gcct                                                24

<210> SEQ ID NO 7
<211> LENGTH: 19

```
<212> TYPE: DNA
<213> ORGANISM: Artificial Sequence
<220> FEATURE:
<223> OTHER INFORMATION: Synthetic oligonucleotide primer

<400> SEQUENCE: 7
gatgagtgta ttgtcatcc                                            19

<210> SEQ ID NO 8
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 8
aacgtagaag agaatggc                                             18

<210> SEQ ID NO 9
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 9
ggactattgt ctaaacaatt tccccgcaag tgaaatctcc tccg                 44

<210> SEQ ID NO 10
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 10
ggttattcga tttctaaatc gcctgggaca agatactcat ctgc                 44
```